US005820564A

United States Patent [19]

Slayton et al.

[11] Patent Number: 5,820,564

[45] Date of Patent: Oct. 13, 1998

[54] METHOD AND APPARATUS FOR SURFACE ULTRASOUND IMAGING

[75] Inventors: Michael H. Slayton, Tempe, Ariz.; Young-Hwan Cho, Seoul, Rep. of Korea; Peter G. Barthe, Phoenix, Ariz.

[73] Assignees: Albatross Technologies, Inc., Mesa, Ariz.; Medison, Co., Ltd., Seoul, Rep. of Korea

[21] Appl. No.: 766,083

[22] Filed: Dec. 16, 1996

[51] Int. Cl.[6] .......... A61B 8/00

[52] U.S. Cl. .......... 600/459; 600/472

[58] Field of Search .......... 128/916, 663.01, 128/662.06, 662.03, 661.01, 660.09; 600/472, 463, 459, 447, 445

[56] References Cited

U.S. PATENT DOCUMENTS

| | | | |
|---|---|---|---|
| 5,305,756 | 4/1994 | Entrekin et al. | 128/660.09 |
| 5,503,152 | 4/1996 | Oakley et al. | 128/661.01 |
| 5,577,507 | 11/1996 | Snyder et al. | 128/663.01 |
| 5,655,535 | 8/1997 | Friemel et al. | 128/916 X |
| 5,704,361 | 1/1998 | Seward et al. | 128/916 X |

OTHER PUBLICATIONS

Talbert, D.G. "An Add–on Modification for Linear Array Real Time Ultrasound Scanners to Produce 3D Displays", UTS Int'l. 1977 Brighton, England (Jun. 28–30, 1977) pp. 57–67.

*Primary Examiner*—Francis Jaworski
*Attorney, Agent, or Firm*—Snell & Wilmer, L.L.P.

[57] ABSTRACT

An ultrasonic imaging apparatus is suitably configured such that certain ultrasound beams from a probe are diffused perpendicular to the scanning direction to thereby enable an ultrasonic image to be produced which approximates a surface image while certain other ultrasound beams are focused to thereby enable a two-dimensional ultrasonic image to be produced. A conventional ultrasonic imaging apparatus and process can be used.

9 Claims, 8 Drawing Sheets

METHOD AND APPARATUS FOR SURFACE ULTRASOUND IMAGING

BACKGROUND OF THE INVENTION

1. Field of the Invention

The present invention relates generally to an ultrasonic diagnostic method and apparatus, and more specifically to a method and apparatus which is adapted to enable a surface imaging of a subject under examination.

2. Description of the Related Art

Typically, ultrasound probes are suitably configured as is well known to enable collection of data which can be suitably manipulated to obtain data relating to biological organs, tissues and the like for diagnostic and imaging applications. In certain applications it is desirable to collect data which enables production of a three-dimensional image of the region under examination. For example, in conducting an ultrasound exam on a fetus it may be desirable to enable production of a image which approximates a surface image, as well as a subsurface image.

Prior art methods and apparatus exist to enable production of a three-dimensional image. For example, when a 3-D region of a subject under examination is scanned such that the focused ultrasound beams can be subjected to 3-D processing, a three-dimensional image approximating a surface image can be obtained. However, unless a very large-scale signal processor is utilized, real time processing, and thus, real time imaging is not readily obtainable.

Other apparatus are known; however, such are complex and/or require relatively complex data manipulation technologies. For example, in U.S. Pat. No. 5,417,219 issued May 23, 1995, to Takamizawa et al., an ultrasonic diagnostic apparatus is disclosed which purports to enable real-time 3-D ultrasound imaging. In one embodiment, Takamizawa et al. disclose a probe adapter which is mounted on an ultrasonic probe to diffuse ultrasound beams. In accordance with this embodiment, the adaptor serves to diffuse the ultrasound beams in the slice direction perpendicular to the scanning direction, such that wide ultrasound beams enable scanning of a three-dimensional region. In a second embodiment Takamizawa et al. disclose a two-dimensional array type of ultrasonic probe in which a plurality of piezoelectric transducers are arrayed along the channel direction (Y direction) and the slice direction (X direction). As disclosed, by introducing a time delay in each of received signals from the plurality of transducers, the ultrasound beam is caused to diffuse in the slice direction.

While each of these disclosed embodiments purport to enable the creation of a desired 3-D image, each pose various undesirable obstacles. For example, in accordance with the second disclosed embodiment a complex delay system is disclosed which tends to inhibit the use of the probe for simultaneous 2-D imaging. Moreover, the 2-D array disclosed is expensive. Similarly in connection with the first disclosed embodiment, with use of the disclosed adaptor, simultaneous 2-D imaging is also not available, and use of such an adaptor, can be unduly complex and cumbersome.

As will be appreciated by those skilled in the art, there is thus a need for a method and apparatus which enables the simultaneous display of both a two-dimensional and a three-dimensional image of the region under examination in a cost effective and convenient manner.

SUMMARY OF THE INVENTION

The present invention addresses this need not filled by prior art methods and/or apparatus in providing a method and apparatus in which a probe is spatially configured to enable the collection of data suitable for the substantially simultaneous, real-time display of both 2-D and 3-D images of the region under examination.

These and other advantages of a system according to various aspects of the present invention will be apparent to those skilled in the art upon reading and understanding the following detailed description with reference to the accompanying drawing figures.

BRIEF DESCRIPTION OF THE DRAWING FIGURES

The subject matter of the invention is particularly pointed out and distinctly claimed in the concluding portion of this specification. Preferred embodiments of the invention, however, both as to organization and method of operation, may best be understood by reference to the following description taken in conjunction with the claims and the accompanying drawing figures, in which like numerals denote like elements and:

DETAILED DESCRIPTION OF EXEMPLARY EMBODIMENTS

While the way in which the present invention addresses the disadvantages of the prior art will be described in greater detail hereinbelow, in general, in accordance with various aspects of the present invention a 1.5 to a 2-dimensional array is utilized to enable substantially simultaneous display of two-dimensional and three-dimensional images of the region under examination. Although the way in which a probe in accordance with the present invention may be configured may vary, as will be described herein, in each case various piezoelectric elements are separately activated to generate signals which can be collected and manipulated to produce both two-dimensional and three-dimensional images.

Figure 1:
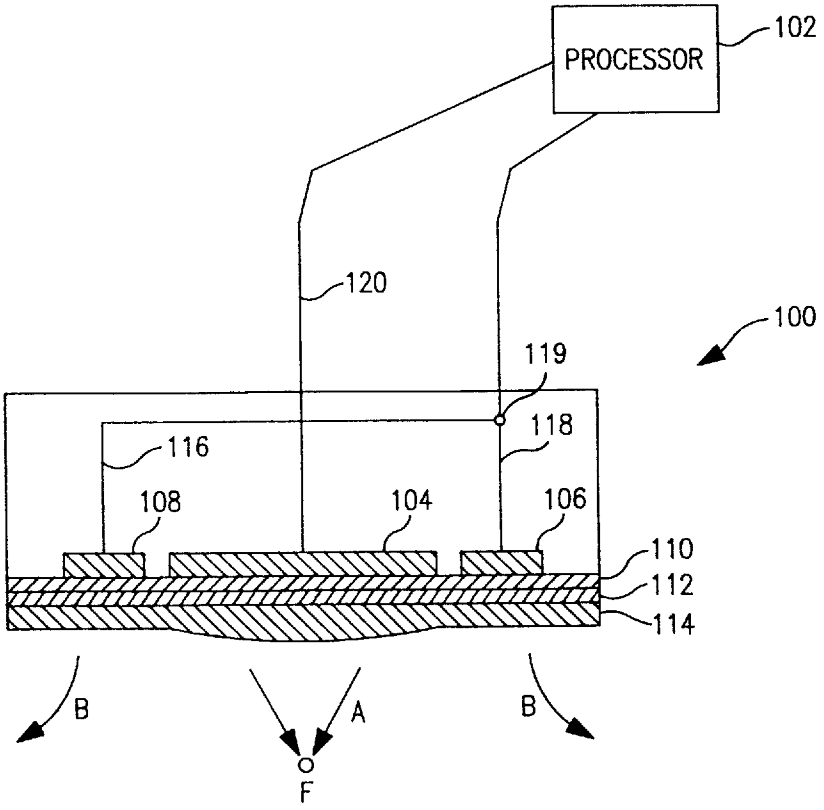
FIG. 1 is a cross-sectional view of the principle probe components of an ultrasound probe in accordance with a first embodiment of the present invention.

Referring now to FIG. 1, in accordance with a first embodiment of the present invention, a probe 100 includes as its principle elements a central piezoelectric element 104, respective inter piezoelectric elements 106, 108, suitable matching layers 110, 112 and a compound lens 114. As shown, elements 108, 106, 104 are suitable electrically connected by respective connectors 116, 118 and 120 to a probe system (not shown) of conventional design configuration. While not shown in its entirety, it should be appreciated that probe 100 can be suitably configured as a conventional ultrasonic probe, and that these principle components arranged in any suitable housing (also not shown). Connectors 116 and 118, which are suitably attached to elements 108 and 106, in accordance with one aspect of the present invention may be suitably connected such as at a connection 119 such that elements 106 and 108 are electrically coupled; connector 120 is not so connected, but rather, is preferably individually wired. Alternatively, each of elements 104, 106 and 108 may be separately wired, with "connection" of the input/output of elements 106, 108 being handled by the processor 102.

As will be appreciated, in construction of probe 100, probe 100 may suitably comprise a plurality of each type of element 104, 106, 108, as may be desired for a particular application. As will be readily appreciated by those skilled in the art, preferably probe 100 is constructed as an array of piezoelectric elements, such as is shown in part in FIG. 2. In accordance with a preferred aspect of the present invention, for example, probe 100 includes 128×3 array of elements 104, 106, 108. Other array configurations which are now known or can hereafter be devised from this disclosure may also be employed in the context of the present invention.

As shown in FIG. 1, probe 100 includes piezoelectric elements 104, 106, 108 each of which evidence a substantially flat portion to which respective electrical connectors 120, 118 and 116 are attached. As will be appreciated, such electronics are provided to connect the elements to the system control electronics (not shown in the figure). The other, or front, face of each of elements 104, 106, 108 is also configured to be substantially flat and is suitably configured as the ultrasound transmitting/receiving zone attached to the front face of each of elements 104, 106, 108 are matching layers 110,112. It should be appreciated that one or more matching layers may be utilized, each being of a conventional design and composition. Specifically, conventional acoustic transducers are typically provided with some kind of a matching layer which is typically made of a loaded epoxy, such as an aluminum powder and epoxy or other suitable material. Other now known or hereafter devised matching and backing layers may also be employed.

As will be appreciated by those skilled in the art, in accordance with various aspects of the present invention, the piezoelectric elements are arranged in the form of a one and one-half to two-dimensional array, the one and one-half array being, in effect, a subset of the category of 2-D array probes. Lens 114 is suitably configured as a compound lens to suitably focus or defocus the ultrasound beam transmitted and/or received from each piezoelectric element. In general, as will be explained in greater detail hereinbelow, compound lens 114 preferably includes multiple foci to accomplish this objective.

In accordance with various aspects of a first embodiment of the present invention, lens 114 is suitably configured as a convex surface in the region of element(s) 104 to enable focusing of the beam created through isonation of element 104, such that, as will be described in greater detail hereinbelow, conventional 2-D imaging can be obtained and displayed. In contrast, lens 114 is suitably configured to evidence a substantially flat surface in the region of elements

106 and 108 such that, as will be described in greater detail hereinbelow, surface or 3D imaging is obtained through appropriate isonation of elements 106 and 108.

Figure 3B:
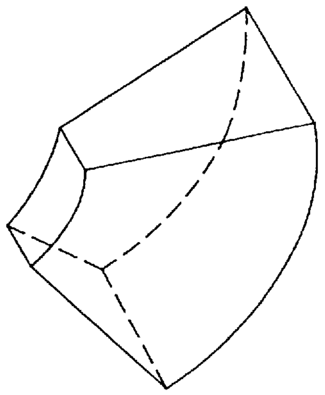
FIGS. 3A and 3B are depictions of a two-dimensional scan region and a three-dimensional scan region, respectively.
Figure 3A:
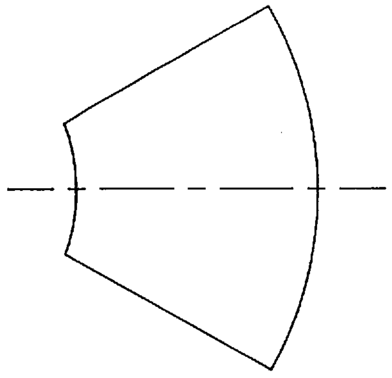

Lens 114 preferably comprises a low acoustic impedance material or combination thereof, for example, a material having an acoustic impedance of less than about 1.5 Mrayl and a speed of sound less than about 1500 M/sec. Exemplary materials include various RTV rubbers and urethane materials. In accordance with various aspects of the present invention, lens 114, as will be explained in greater detail below, is suitably configured to focus or diffuse (defocus) ultrasound beams passing therethrough. In the context of the present invention, the term "focus" is used in its usual sense to refer to the focussing of an ultrasound beam from probe 100 onto a focal point at a distance from the probe, with diffusion of the beam occurring at depths beyond the focal point. Focusing of the beam, as will be appreciated, enables formation of a two-dimensional scan region, such as is shown schematically in FIG. 3A. On the other hand, in the context of the present invention, "diffusion" refers to a defocusing of the ultrasound beam from probe 100 to increase the width of the ultrasound beam. Thus, instead of focusing the ultrasound beam at a focal point, the beam is instead diffused in a direction substantially perpendicular to the scanning or azimuth direction. The wide ultrasound beams that are thereby produced enable creation of a three-dimensional scan region, such as is shown in FIG. 3B. By widening the ultrasound beam in this manner, echoes received by probe 100 can be accumulated and manipulated so as to approximate a surface image.

Probe 100 is configured to be suitably attached to an ultrasonic diagnostic apparatus which is preferably of a conventional design and function and as such includes appropriate signal transmitting, receiving and processing circuitry. As such devices are well-known, the description of such is not herein described. However, for completeness, FIG. 4 and the description of FIG. 4 of U.S. Pat. No. 5,417,219 relating to the design and function of an ultrasonic diagnostic apparatus is incorporated herein by reference.

With probe 100 suitably connected to an ultrasonic diagnostic apparatus, probe 100 can be utilized to transmit and receive ultrasound beams such that conventional procedures used, for example, for producing usual two-dimensional images, can be used for producing both a two-dimensional image and a three-dimensional image which approximate a surface image.

Figure 2:
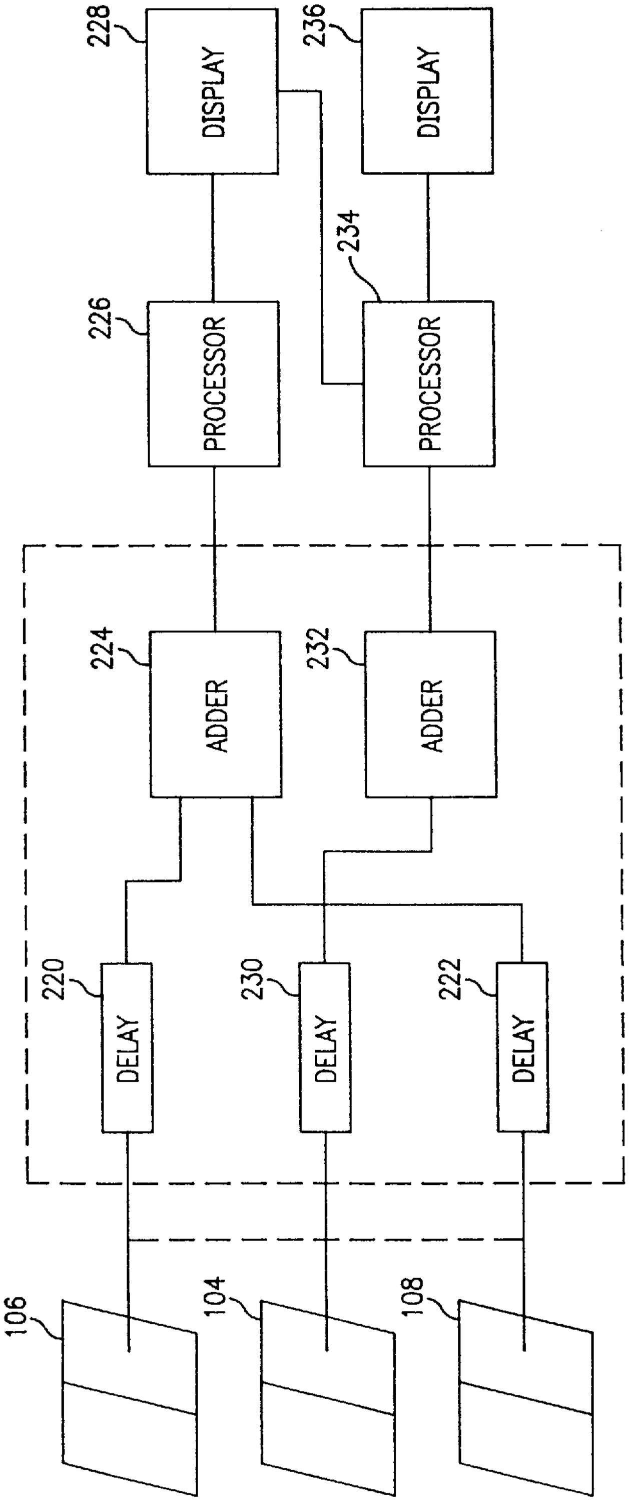
FIG. 2 is a block diagram of an exemplary delay circuit which can be utilized in accordance with a probe configured as shown in FIG. 1.

With reference to FIG. 2, the operation of a probe in accordance with this present invention, such as that shown in FIG. 1, will now be described. As previously noted, probe 100 is suitably connected to a conventional diagnostic device (processor) such that a transmit control circuit is suitably activated to produce a scanning ultrasound beam through excitation of the various piezoelectric elements comprising probe 100. Specifically, the transmission control system suitably comprises a pulse generator for generating a rate pulse determining the repetition period of ultrasound pulses, transmit delay circuits, each providing a delay time inherent in the corresponding one of the simultaneously excited transducers to that rate pulse, and exciting circuits each applying an exciting pulse to the corresponding transducer of the simultaneously excited transducer set via an electronic switch circuit at the time of receipt of a rate pulse from the corresponding transmit delay circuit to thereby cause that transducer to produce an ultrasonic wave.

In accordance with a preferred aspect of the present invention, however, the processor is configured to simultaneously produce two ultrasonic waves A and B, one emanating from elements 104 and the other from elements 106 and 108 (See FIG. 1). Reflected echoes from wave A are suitably manipulated to create a 2-D image, whereas, as previously noted, reflected echoes from wave B are suitably manipulated to create a 3-D or surface image.

Specifically, reflected waves from wave B are reflected from the surface of the object under examination, e.g. the fetus and are received by the same transducers as at the transmission time. Received signals by the transducers are furnished with respective inherent time delays in the respective receive delay circuits 220, 222 then added together in an adder 224. An output signal of the adder 224 is fed via a processor 226 where an image signal is detected.

In a similar fashion, waves reflected from wave A, emanating from elements 104, are caused to focus onto a focal point F within the surface of the region under examination. Received signals are provided with an inherent delay by the delay circuit 230 and are added together in an adder 232. The added signals are suitably processed by the processor 234 and can then be suitably displayed as a 2-D image in display 236 and/or display 228. In this manner, substantially simultaneous, real time display of both 2-D and 3-D images can be obtained.

Figure 5:
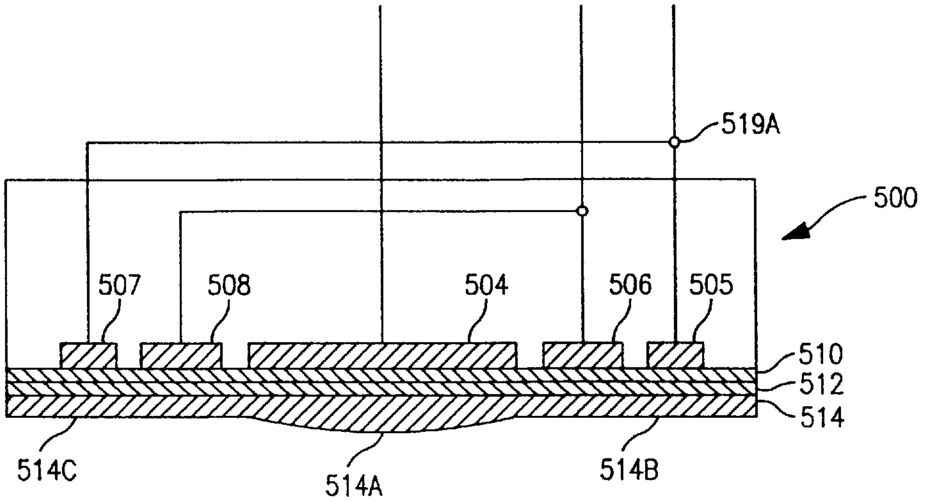
FIG. 5 is a cross-sectional view of the principle probe components of an ultrasound probe in accordance with yet another embodiment of the present invention.

Having now described the basic operation of a probe 100 in accordance with the present invention, various modifications will readily occur to those skilled in the art. In an attempt to illustrate some, but obviously not all of these various modifications, various alternative embodiments will now be described. It should be appreciated, however, that these modifications are set forth or arranged in elevational connection. In FIG. 5, probe 500 is similar to probe 100 except that additional outlying elements 505, 507 are added and appropriately connected, such as at connection 519A. As with probe 100, a lens 514 is suitably affixed to probe 500 with suitable respective matching layers 510, 512, separating elements 504–508 and lens 514. As with lens 114, lens 514 is suitably configured to evidence a substantially convex central portion 514A and respective outlying substantially flat portions 514B and 514C.

Figure 6:
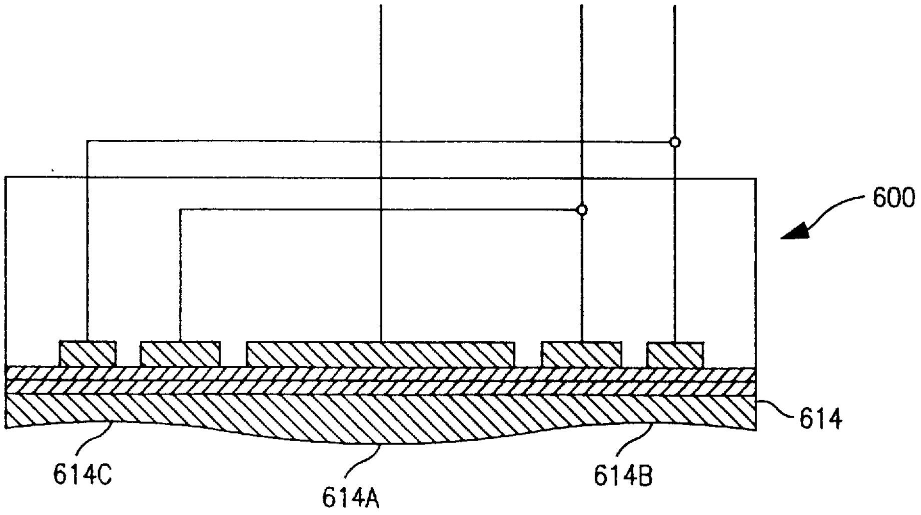
FIG. 6 is a cross-sectional view of the principle probe components of an ultrasound probe similar to that shown in FIG. 5 but in accordance with still another embodiment of the present invention.

Probe 600, shown in FIG. 6, is similar to that shown in FIG. 5, except that like probe 400, lens 614 of probe 600 is suitably configured to evidence an outer surface including a convex central portion 614A and respective outlying concave portions 614B and 614C.

In certain applications, increasing the number of elements utilized to provide the 3-D image may be beneficial, for example, to increase the field of view of the subject probe. It should be appreciated, however, that the various embodiments shown herein are illustration only and should therefore not be viewed as limiting the invention herein disclosed.

Figure 4:
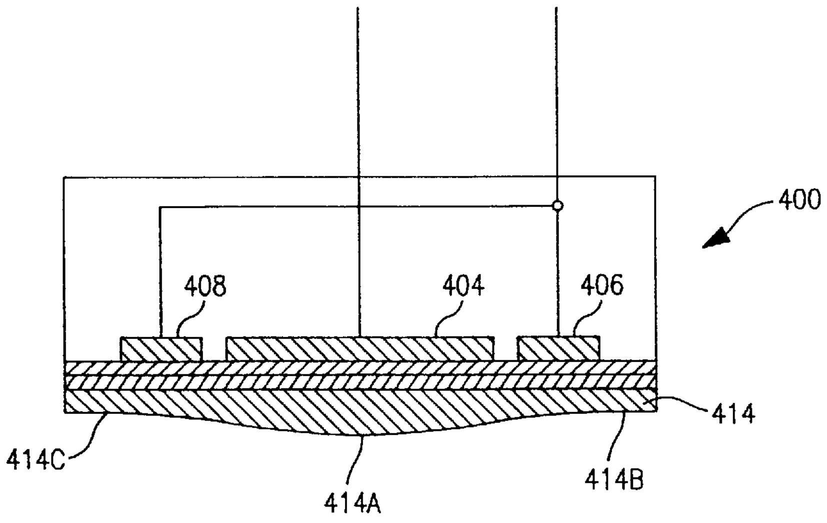
FIG. 4 is a cross-sectional view of the principle probe components of an ultrasound probe in accordance with another embodiment of the present invention.

With reference to FIG. 4, a probe 400 is illustrated, which while similar to probe 100, includes a lens 414 which is of a different configuration. Specifically, in accordance with a preferred aspect of this embodiment of the present invention, lens 414 is suitably configured to evidence an outer surface having a convex portion 414A and respective concave portions 414B and 414C. Convex portion 414A suitably focuses the ultrasonic beam emanating from piezoelectric elements 404, while concave portions 414B and 414C suitably diffuse (defocus) the ultrasonic beam emanating from respective piezoelectric elements 406 and 408, respectively.

Referring now to FIG. 5, a further probe 500 in accordance with various aspects of the present invention is illustrated. Probe 500 suitably includes a central piezoelectric element 504 with several smaller piezoelectric elements 505, 506, 507 and 508.

Figure 7:
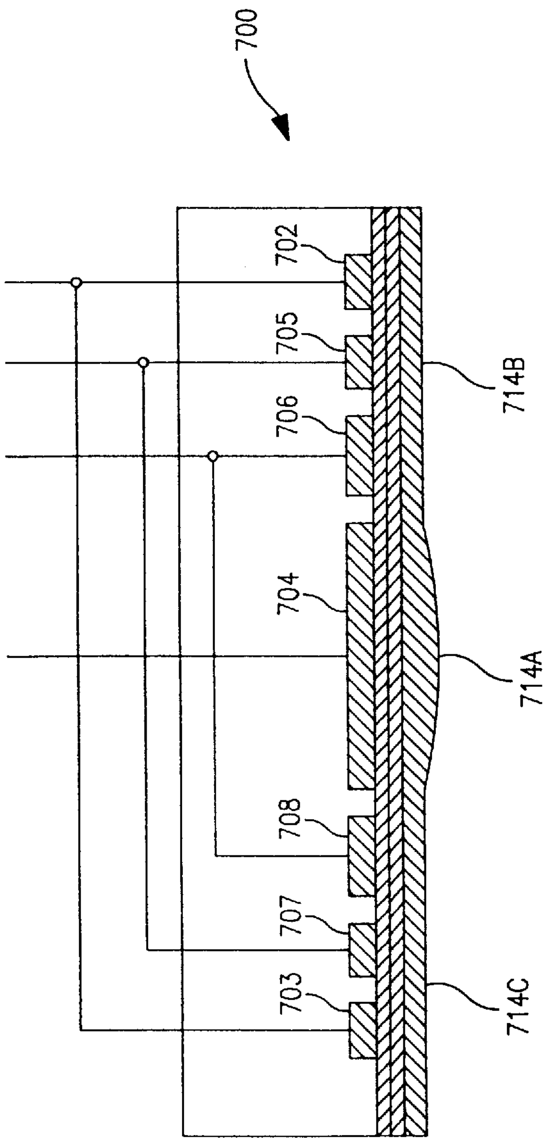
FIG. 7 is a cross-sectional view of the principle probe components of an ultrasound probe in accordance with yet another embodiment of the present invention.
Figure 8:
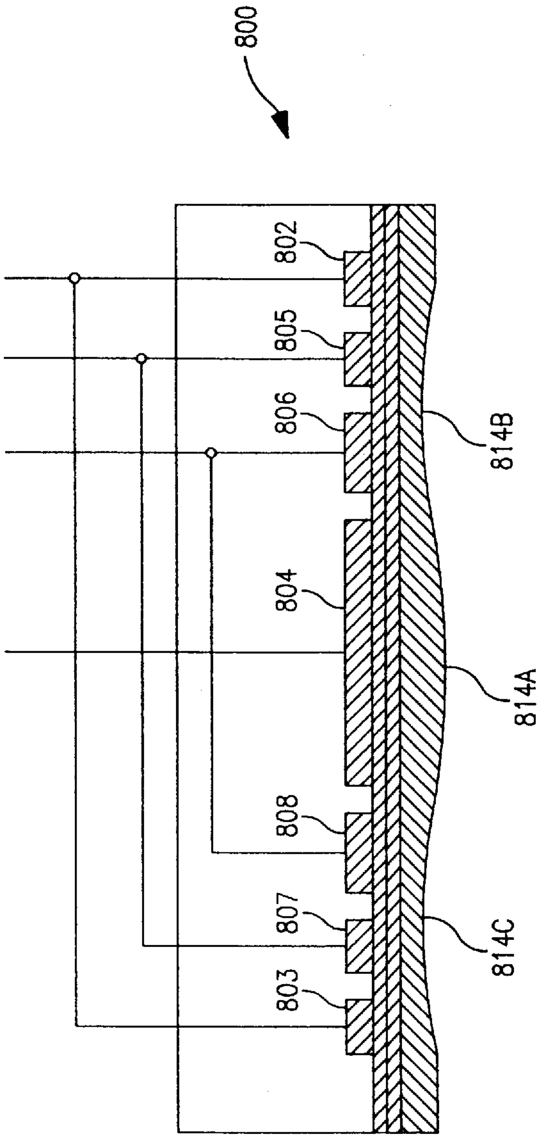
FIG. 8 is a cross-sectional view of the principle probe components of an ultrasound probe similar to that shown in FIG. 7 but in accordance with still another embodiment of the present invention.

Accordingly, in accordance with various other embodiments of the present invention, the number of outlying piezoelectric elements is suitably increased. For example, FIGS. 7 and 8 show probes 700 and 800, each including a central element 704 or 804 surrounded by additional piezoelectric elements 702, 703, 705, 707, 706, 708 (for probe 700) or 802, 803, 805, 807, 806, 808 (for probe 800). In probe 700, a lens 714, like lenses 114 and 514 includes respective substantially flat regions 714B and 714C and a central convex region 714A, whereas in probe 800, a lens 814, like lenses 414 and 614, includes respective concave portions 814B and 814C and a central convex region 814H.

As shown in FIGS. 5–8, when additional outlying piezoelectric elements are utilized, the dimensions of the furthest outlying elements may be increased or decreased (as is illustrated), as may be desired. For example, depending on the particularly desired clinical application, it may be advantageous to change the field of view or the focusing requirements of a particular probe configuration. Accordingly, the outlying elements may be increased in size or decreased in size to change the focusing required or field of view, as may be appreciated.

It should be understood that the foregoing description relates to preferred exemplary embodiments of the invention, and that the invention is not limited to the specific forms shown herein. Various modifications may be made in the design and arrangement of the elements set forth herein without departing from the scope of the invention as expressed in the appended claims. For example, there will be immediately obvious to those skilled in the art many modifications of structure, arrangements, proportions, the elements, materials and components, used in the practice of the invention which are particularly adapted for a specific environment and operating requirements without departing from those principles. These and other modifications in the design, arrangement, and application of the present invention as known or hereafter devised by those skilled in art are contemplated by the following claims.

We claim:

1. An ultrasonic probe comprising:

a first set of piezoelectric elements for electro-acoustic conversion to produce a first ultrasonic beam;

a second set of piezoelectric elements for electro-acoustic conversion to produce a second ultrasonic beam;

wherein said first ultrasonic beam and said second ultrasonic beam are directed upon a region under examination; and a lens configured for acoustic communication with said first and said second ultrasonic beams, wherein said lens is configured to focus said first beam at a predetermined focal depth in an elevation direction and wherein said lens is configured to diffuse said second beam in said elevation direction, said elevation direction being in a plane substantially perpendicular to a scanning direction.

2. The probe of claim 1 wherein said lens comprises a focusing portion and at least one diffusing portion, said diffusing portion configured to diffuse ultrasonic waves transmitted from said piezoelectric elements in a plane substantially perpendicular to the scanning direction.

3. An ultrasonic imaging or diagnostic apparatus comprising:

an ultrasonic probe comprising a one and one-half-dimensional or two-dimensional array of piezoelectric elements;

a compound lens configured for acoustic communication with said piezoelectric elements;

excitation means for exciting said piezoelectric elements to transmit ultrasonic waves;

receiving means for receiving reflected waves from reflectors within a subject under examination through said piezoelectric elements;

processing means for processing said reflected waves to produce a two-dimensional image and to produce a three-dimensional image; and displaying means for displaying said images.

4. The apparatus of claim 3 wherein said probe comprises a one and one-half dimensional array of pizeoelectric elements.

5. The apparatus of claim 3 wherein said probe comprises a two-dimensional array of pizeoelectric elements.

6. The apparatus of claim 3 wherein said compound lens comprises a focusing portion and at least one diffusing portion.

7. The apparatus of claim 6 wherein said lens focusing portion exhibits a first focal length and said at least one lens diffusing portion exhibits a second focal length, said first focal length being different from said second focal length.

8. The apparatus of claim 7 wherein said lens focusing portion includes a substantially convex portion and said lens diffusing portion includes at least one portion which is substantially flat.

9. The apparatus of claim 7 wherein said lens focusing portion includes a substantially convex portion and said lens diffusing portion includes at least one substantially concave portion.

* * * * *